(12) United States Patent
Könemann et al.

(10) Patent No.: US 6,986,811 B2
(45) Date of Patent: Jan. 17, 2006

(54) PERYLENE DERIVATIVES AND THEIR APPLICATION AS DISPERSANTS

(75) Inventors: Martin Könemann, Mannheim (DE); Ulrike Hees, Mannheim (DE); Valerie Pierre, Berkeley, CA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/759,206

(22) Filed: Jan. 20, 2004

(65) Prior Publication Data

US 2004/0194665 A1 Oct. 7, 2004

(30) Foreign Application Priority Data

Jan. 31, 2003 (DE) ................. 103 03 916

(51) Int. Cl.
- C08K 5/00 (2006.01)
- C07D 221/22 (2006.01)
- C08G 73/02 (2006.01)
- C09B 67/38 (2006.01)
- C08J 3/20 (2006.01)

(52) U.S. Cl. ............ 106/493; 106/498; 546/37; 546/38; 549/232

(58) Field of Classification Search ........ 106/493, 106/498; 546/37, 38; 549/232

See application file for complete search history.

(56) References Cited

U.S. PATENT DOCUMENTS

| | | | | |
|---|---|---|---|---|
| 4,594,420 A | * | 6/1986 | Spietschka et al. | 546/29 |
| 4,599,408 A | * | 7/1986 | Spietschka et al. | 544/125 |
| 4,709,029 A | * | 11/1987 | Spietschka et al. | 544/125 |
| 5,472,494 A | | 12/1995 | Hetzenegger et al. | |
| 5,900,490 A | * | 5/1999 | Feiler | 549/232 |
| 5,958,129 A | * | 9/1999 | Urban et al. | 106/498 |
| 6,063,181 A | * | 5/2000 | Bohm et al. | 106/493 |
| 6,093,834 A | * | 7/2000 | Feiler | 549/232 |
| 6,136,976 A | * | 10/2000 | Boehm et al. | 544/314 |
| 6,143,905 A | * | 11/2000 | Bohm et al. | 549/232 |
| 6,409,816 B1 | | 6/2002 | Weber et al. | |
| 6,413,309 B1 | * | 7/2002 | Weber et al. | 106/493 |
| 6,464,902 B1 | * | 10/2002 | Gaynor et al. | 252/600 |
| 6,784,301 B2 | * | 8/2004 | Hackmann et al. | 549/232 |

\* cited by examiner

*Primary Examiner*—Anthony J. Green
(74) *Attorney, Agent, or Firm*—Oblon, Spivak, McClelland, Maier & Neustadt, P.C.

(57) ABSTRACT

The present invention relates to substituted perylene derivatives in which the substituent has a sterically stabilizing and/or electrostatically stabilizing effect. The perylene derivatives of the invention are particularly suitable as pigment dispersants. The present invention additionally relates to pigment preparations in which the perylene derivatives of the invention are used.

13 Claims, No Drawings

PERYLENE DERIVATIVES AND THEIR APPLICATION AS DISPERSANTS

The present invention relates to perylene derivatives having sterically stabilizing or electrostatically stabilizing radicals and also to the use of these perylene derivatives as pigment dispersants. The present invention further provides pigment preparations which comprise the perylene derivatives of the invention as pigment dispersants. The present invention additionally relates to a process for preparing the pigment preparations of the invention and also to their use as colorants for pigmenting high molecular mass organic materials. The present invention also provides pigment dispersions which comprise at least one perylene derivative of the invention.

The incorporation of solids into liquid media requires high mechanical forces. In order to lessen these dispersing forces it is usual to use dispersants which facilitate the incorporation process. Dispersants are also used in pigment preparations.

Pigment preparations are combinations of pigments with pigment dispersants that are structurally analogous to pigments. The pigment dispersants are added to the pigments in order to facilitate their dispersion in the application media and in order to enhance the rheological and coloristic properties of the pigments. The viscosity of the highly pigmented application media is lowered and the flocculation of the pigment particles is reduced. By this means it is possible, for example, to increase the transparency and the gloss. Inadequate dispersing is manifested in a rise in viscosity in liquid systems, losses of gloss and shifts of shade in coating materials and coatings, and insufficient development of color strength.

There are a multiplicity of proposals aimed at improving the rheological and coloristic properties of pigments through addition of pigment dispersants, not all of which, however, lead to the anticipated result.

EP-A 1 029 899 describes pigment preparations comprising a diketopyrrolopyrrole pigment plus a perylene pigment dispersant in the form of a carboxylic diimide. These pigment preparations do not meet the desired rheological and coloristic requirements and are not universally applicable.

DE-A 43 25 247 describes pigment preparations which in addition to at least one organic pigment and, if desired, further additives include a perylene derivative as pigment dispersant. These perylene derivatives are at least singly substituted, the substituent being composed of an anionic sulfonic acid radical satisfied with a cation. The species used as cation is alternatively a proton, a metal cation or an ammonium cation. These perylene derivatives, accordingly, are salts. The pigment dispersants described, based on perylene compounds, likewise exhibit coloristic and rheological deficiencies. Furthermore, in aqueous media the pigment dispersants have a low pH, which in certain applications of the pigment preparations is a drawback.

It is an object of the present invention to provide pigment preparations which overcome the stated drawbacks of the prior art in respect of coloristics, rheology, and universal applicability. A further object was to provide pigment preparations which have a higher pH in aqueous media than the prior art pigment preparations.

We have found that these objects are achieved in accordance with the invention by pigment preparations which in addition to a pigment comprise one or more perylene derivatives of the formula (I).

The present invention accordingly provides perylene derivatives of the formula (I)

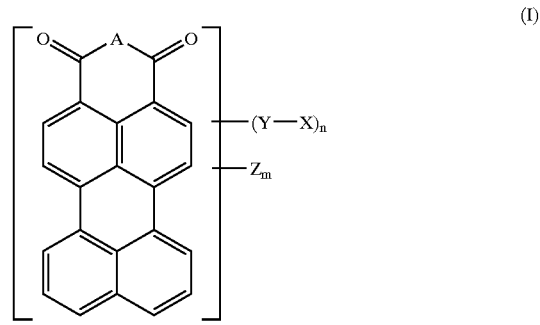

where
A has the definition O, $CH_2$ or $NR^1$ with $R^1$ being H, aryl, aralkyl, heteroaryl, cycloalkyl, $C_1$–$C_{22}$ alkyl,
Y, each identical or different, is —$CO_2$, —$CONR^2$, —$SO_3$ or —$SO_2NR^2$, $R^2$ being H, aryl, aralkyl, heteroaryl, cycloalkyl, $C_1$–$C_{22}$ alkyl, preferably $C_1$–$C_6$ alkyl, alkylamine, in which the amine function may if desired carry one or more further substituents and may be part of a polyamine,
X, each identical or different, is a predominantly sterically stabilizing and/or electrostatically stabilizing substituent,
Z, each identical or different, represents where present one or more further substituents, selected from the group consisting of alkyl, alkoxy, and aryloxy groups and halogens, especially chlorine and bromine,
n is an integral number greater than or equal to 1, and
m is an integral number greater than or equal to 0.

The invention accordingly provides perylene derivatives which through selection of suitable substituents are either sterically and/or electrostatically stabilizing.

Sterically Stabilizing Substituents

Sterically stabilizing substituents are understood in accordance with the invention to be substituents through which the pigment dispersant attaches firmly to the pigment surface, the pigment dispersant substantially completely covers the surface of the pigment, and the solvated portion reaches into the respective medium and forms a boundary layer of sufficient thickness. For details, refer to the publications "Science and Technology of Pigment Dispersions—A four day post graduate intensive course presented by Institute of Materials Science", pp. 309 to 328, and "Pigment Dispersants for non-aqueous systems", Interlaken, Switzerland, Jun. 14–18, 1999, and "A new graft polymer pigment dispersant synthesis" by J. S. Simms, Progress in Organic Coatings, 35, 1999, pp. 205 to 214, the entire disclosure content of which is included by reference in the present invention. The sterically stabilizing substituents are substantially polymer radicals. These polymer radicals preferably carry at least one group having affinity for binder or for solvent. In accordance with the invention a group having affinity for binder or for solvent is understood to be a functional group of the polymers that renders the polymer substantially soluble in a binder or solvent, respectively. A binder for the purposes of the invention comprehends polymeric compounds which join substances of like or different type to one another. Depending on their structure, a distinction is made between organic and inorganic or between natural and synthetic binders. The binding, in other words the joining together of substances, is accomplished through physical drying, through solidification or a sharp increase in viscosity, through chemical reaction or through hydration. Numerous binders suitable in accordance with the invention are known from the prior art. Examples that may be given of binders suitable in accordance with the invention include, in general, alkyd-melamine resin varnish and acrylic-melamine resin varnish with melamine as the group having affinity for binder.

The corresponding polymers of the polymer radicals used in accordance with the invention preferably include at least one group which can be reacted with a carbonyl chloride or with a sulfonyl chloride of a perylene derivative. Examples of groups of the polymers that are suitable in accordance with the invention are free OH, NH or SH groups. In the reaction the sterically stabilizing polymers are bonded covalently to the perylene derivative.

Examples of sterically stabilizing substituents suitable in accordance with the invention include long-chain alkyl radicals, which are preferably joined by way of functional groups to the carbonyl chlorides and/or sulfonyl chlorides of the perylene derivatives. By long-chain alkyl radicals are meant in this context, generally, $C_4$–$C_{64}$ alkyl radicals, preferably $C_4$–$C_{32}$ alkyl radicals, more preferably $C_4$–$C_{18}$ alkyl radicals. In specific embodiments of the present invention they are $C_{12}$ or $C_{18}$ alkyl radicals. The alkyl radicals may additionally, where appropriate, be carriers of further substituents of any kind, with the proviso that these substituents do not disrupt the sterically stabilizing function of the alkyl radicals.

In one preferred embodiment of the present invention the sterically stabilizing substituents are selected from the group consisting of polymers based on alkylene oxides, polymers based on polyesters, polymers based on polyacrylates, polymers based on alkyl sulfides, and polymers based on alkyl compounds. These polymer radicals too may where appropriate be carriers of further substituents of any kind, with the proviso that these substituents do not disrupt the sterically stabilizing function of the polymer radicals.

One example of a sterically stabilizing polymer radical suitable in accordance with the invention can be derived from a polymer which is preparable by ring-opening polymerization of ε-caprolactone with dodecylsulfonic acid and subsequent grafting with polyethyleneimine. Instead of polyethyleneimine it is also possible in accordance with the invention to use other polymers, such as polyvinylamines or copolymers with ethyleneimine and vinylamine, for example. In accordance with the invention it is possible in addition to ε-caprolactone to use further polyesters and/or polyacrylates and/or polyurethanes and/or polyalkylene glycols.

Further sterically stabilizing substituents are preferably polymer radicals of crosslinked block polymers. These polymers may where appropriate be linear and where appropriate may be homopolymeric in nature. By polymers which are homopolymeric in nature the invention understands polymers composed of monomers of only one kind. The block polymers are preferably block copolymers with a graduated affinity (solubility) for the binder.

In one particular embodiment of the present invention the sterically stabilizing radicals used are block (co)polymers of the general structure $aX(A)_x\text{-}(B)_y\text{-}bx(C)$ in which the blocks are composed preferably of hyperbranched polymers and/or comb polymers. Comb polymers are understood in accordance with the invention to be polymers having a linear main chain with relatively long, usually aliphatic, side chains at more or less regular intervals. Central to the block (co)polymers is the polymer block B, which can be preferably branched or linear and which where appropriate includes functional groups which allow both attachment of two or more blocks of the polymer A and also of two or more perylene derivatives C. For linking with the polymers A and/or with the perylene derivatives C it is possible where appropriate for additional difunctional or polyfunctional linking components to be incorporated. Alternatively, linking may also take place directly.

Polymers suitable as polymer block A, depending on coating system and solvent, include general polymers of the structure $U\text{-}(M)x\text{-}T$ where U=H, alkyl or initiator radical, M represents one or more repeating units of a polymer, and T is a group by way of which linking of the A block to the B block takes place. T is preferably an oxygen or sulfur atom, an $NR^2$, COO or $CONR^3$ group with $R^2$ and $R^3$ as a radical of any kind. Repeating units M of the polymer are preferably random copolymers, such as free-radical copolymers, for example, which are prepared in general with regulators for adjusting the molecular weight and with functional groups, such as by using mercaptoethanol, functionalized block copolymers, polycondensates, polyadducts, such as polyurethanes, for example, and polyalkylene glycols. The repeating units M may where appropriate be carriers of further substituents, with the proviso that these substituents do not disrupt the sterically stabilizing function of the block copolymers.

The B block is preferably polyfunctional, allowing attachment of two or more blocks (ax with $a \geq 1$) A and also two or more blocks (bx with $b \geq 1$) C. The limiting case where a=1 and y=0 also includes, however, a simple construction with A=polyethylene or alkyl, with linkage by OH groups or further groups able to react with a carbonyl chloride and/or sulfonyl chloride. y=0 here means that there is a direct linkage of the blocks A and C. This may result preferably, but not necessarily, in a comb structure or else in graft copolymers. The B block can be linear or branched and can be composed, for example, of polyethyleneimines, homopolymers and copolymers of polyvinylamine, poly (meth)(alkyl) acrylates, polyvinyl compounds and their copolymers, polyolefins, polyethylene glycols, polyesters, polytetrahydrofurans, polyethers, polyurethanes with corresponding functionality through incorporation of hydroxyethyl (meth)acrylate, polyvinyl alcohol, etc.

C is a perylene derivative, which is bonded preferably covalently to the B block. The compounds of the invention contain preferably more than one group C per B block (b>1). Perylene derivatives of the invention are, for example, sulfonic esters, carboxylic esters, sulfonamides, and carboxamides.

In the simplest case, A and B can preferably include just a single polymer or copolymer, so that the block structure shrinks to an endgroup functionalization, or else at least a plurality of pigment derivatives are attached to the random copolymer.

Electrostatically Stabilizing Substituents

As regards the electrostatic stabilizing substituents and the way in which this stabilization functions, refer to the publication *"Science and technology of Pigment*

Dispersions—A four day post graduate intensive course presented by Institute of Material Science", pp. 171–208, "Colloid Stability in the DVLD Regime", Interlaken, Switzerland, Jun. 14 to 18, 1999, the entire disclosure content of which is included by reference in the present invention.

By the electrostatically stabilizing substituents are meant, in accordance with the invention, cationic radicals which are bonded covalently to the perylene derivative and include the amino and/or ammonium groups. In order to be able to have an electrostatically stabilizing activity the amino groups must be protonated. Further electrostatically stabilizing substituents are anionic radicals, e.g. sulfonic acids which are deprotonated.

As regards the radicals which carry amine and/or ammonium groups, refer to EP-A 0 864 613, DE-A 199 02 907 and EP-A-1 029 899, the entire disclosure content of which is included in the present invention by reference. All three patent applications describe perylene pigment dispersants substituted by radicals which carry amine and/or ammonium groups. The same radicals are suitable in accordance with the invention.

Further electrostatically stabilizing substituents are substituents of the formula (II)

$$X-Y-NR^4R^5 \quad (II),$$

where $X=NR^6$, O, S and $R^4$, $R^5$, $R^6$, each identical or different, are alkyl, aryl, heteroaryl, H, and $Y=-(CH_2)_n-$ with $n \geq 2$, disubstituted aromatics, disubstituted heteroaromatics. Preferred basic heteroaromatics are imidazolyl, piperidinyl, morpholinyl, pipecolinyl, pyrrolidinyl, pyrazolyl and piperazinyl.

Further preferred electrostatically stabilizing substituents are oligoamines of the general structure:

$$X1-(CH_2)_n-X2-(CH_2)_n-X3,$$

$$X1-(CH_2)_n-X2-(CH_2)_n-X3-(CH_2)_n$$

$$X1-(CH_2)_n-X2-(CH_2)_n-X3-(CH_2)_n-X4-(CH_2)_n \text{ etc.},$$

where X is an amine unit NR* with R*=H, alkyl and n=2 to 12, preferably 2 to 5.

Further electrostatically stabilizing radicals preferred in accordance with the invention are oligo-/polyalkylene glycols of the formula:

$$R^7Z(CH_2-CHR^8-O)_n-R^9,$$

where
$R^7Z=OH$, $NH_2$, SH
$R^8=$ a linear or branched $C_1$–$C_6$ alkyl radical, for example, ethylene glycol or polylene glycol,
$R^9=$ a linear or branched $C_1$–$C_6$ alkyl radical.

The electrostatically stabilizing radicals of the invention are quaternized on their amine functions, preferably with $C_1$ to $C_{18}$ alkyl groups to give ammonium functions, and/or are deprotonated when the radical in question is anionic.

Further electrostatically stabilizing substituents suitable in accordance with the invention are derived from:

a) diamines, especially N,N-dimethyl-p-phenylenediamine, dimethylaminomethylamine, diethylaminoethylamine, 2-ethylhexylaminoethylamine, stearylaminoethylamine, oleylaminoethylamine, dimethylaminopropylamine, diethylaminopropylamine, dibutylaminopropylamine, diethylaminobutylamine, dimethylaminoamylamine, diethylaminohexylamine, 1-diethylamino-4-aminopentane, piperidinomethylamine, piperidinoethylamine, piperidinopropylamine, pipecolinoethylamine, pipecolinopropylamine, imidazolopropylamine, morpholinoethylamine, piperazinoethylamine, 3-cyclohexylaminopropylamine, 3,3'-oxybis(ethyleneoxy)bispropylamine, ethylenediamine, 1,2-propanediamine, 1,3-propanediamine, 2,2-dimethyl-1,3-propanediamine, isophoronediamine, diethylenetriamine, triethylenetetramine, tetraethylenepentamine, pentaethylenehexamine, dipropylenetriamine, N,N-bis(3-aminopropyl)methylamine, tripropylenetetramine, 3-(2-aminoethyl)aminopropylamine, N,N'-bis(3-aminopropyl)ethylenediamine, bis(3-dimethylaminopropyl)-amine, 4,7-dioxadecane-1,10-diamine, 4,9-dioxadodecane-1,12-diamine, 5-amino-1,3,3-trimethylcyclohexane-methanamine, 1,4-bis(3-aminopropoxy)butane.

b) monoamines, especially ammonia, methylamine, ethylamine, n-propylamine, isopropylamine, n-butylamine, sec-butylamine, isopentylamine, n-hexylamine, dimethylamine, diethylamine, dibutylamine, N-ethylbutylamine, β-hydroxyethylamine, β- or γ-hydroxypropylamine, N-methylethanolamine, diethanolamine, 3-(2-hydroxyethylamino)-1-propanol, ethanolamine, diethanolamine, N-(2-hydroxyethyl)aniline, hydroxylamine, hydrazine, 3-ethoxypropylamine, di-(2-methoxyethyl)amine, cyclohexylamine, N-ethylcyclohexylamine, dicyclohexylamine, benzylamine, 2-phenylethylamine, 4-methoxyphenylethylamine, 1-phenyl-3-phenylpropylamine, 2-(3,4-dimethoxyphenyl)ethylamine, aniline, o-toluidine, p-toluidine, N-ethylaniline, 2-(2-aminoethoxy)ethanol, 2-(2-(3-aminopropoxy)ethoxy)ethanol.

In one preferred embodiment of the present invention, n=1 and m=0 in the formula (I) and the perylene derivatives accordingly are of the formula (III),

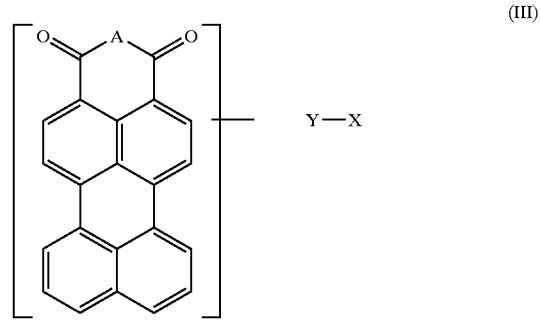

where
A is NH,
Y is —CONH, —SO$_3$ or —SO$_2$NH,
X is a substituent which includes a protonatable amino group, preferably a $C_1$ to $C_{22}$ alkylamine, it being possible for the nitrogen atom of the amine function to be substituted by further alkyl groups and to be part of a polyamine, or is part of a ring system, or
X is $C_1$–$C_{30}$ alkyl or $C_3$–$C_{30}$ alkenyl, it being possible for the carbon chain to be interrupted in each case by one or more groups —O—, —CO—O—, —O—CO— or —S— and each of which may be substituted by $C_1$–$C_6$ alkoxy, amino, hydroxyl, carboxyl groups and halogens.

In another preferred embodiment of the present invention the perylene derivatives of the invention have the formula (IV)

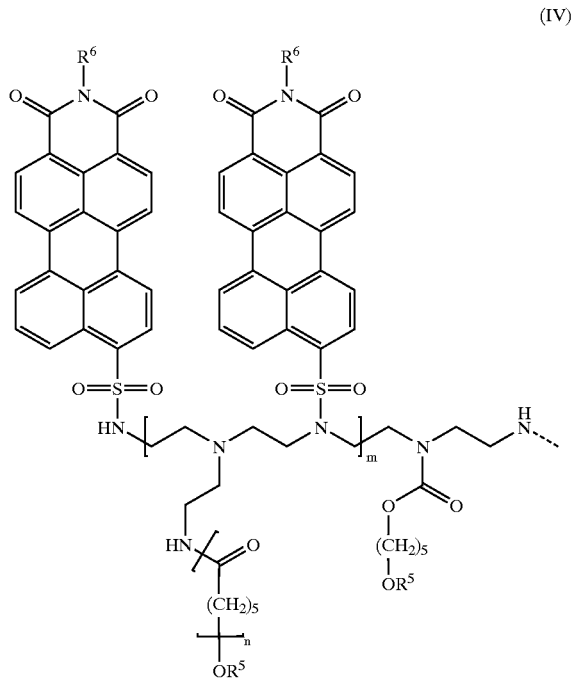

(IV)

where
m is an integral number from 1 to 100,
n is an integral number from 1 to 20,
$R^5$ is $C_{1-64}$-alkyl-$SO_2$, and
$R^6$ is H or $C_1$–$C_6$ alkyl, preferably H or $CH_3$, more preferably H.

The present invention additionally provides a process for preparing the perylene derivatives of the invention. The carboxylic acid and the carbonyl chloride of the perylene derivatives of the invention are prepared by processes which are known per se. The carboxylic acid is prepared in accordance with CAS75:140549j (1971). Starting from this carboxylic acid the carbonyl chloride can be prepared in accordance with the general experimental instructions in *Organikum, Deutscher Verlag der Wissenschaft, Berlin* 1990, 18*th edition*, page 423 ff.

The sulfonyl chlorides of the perylene derivatives of the invention are prepared by sulfochlorination with sulfuryl chloride (preferably 1 to 15 mol. eq., more preferably 8 to 12 mol. eq., based in each case on the perylene derivative) and thionyl chloride (preferably 1 to 2 mol. eq., more preferably 0.8 to 1.2 mol. eq., based in each case on the perylene derivative). Excess chlorosulfonic acid arising in this reaction is removed by filtration and rapid washing with ice-water. Acetone can be used likewise to wash impurities of hydrochloric acid from the solid sulfonyl chlorides.

The sulfonyl chlorides and carbonyl chlorides of the perylene derivatives readily undergo hydrolysis in air under atmospheric conditions and are therefore used quickly or else stored in the absence of moisture.

The carbonyl or sulfonyl chlorides of the perylene derivatives are subsequently reacted with the aforementioned sterically or electrostatically stabilizing substituents to give the corresponding acid amides or esters. Particularly suitable solvents for the reaction include polar solvents, such as DMF, NMP, dimethylacetamide or THF. The reaction takes place preferably in the presence of a hydrochloric acid scavenger base, although no such reagent is absolutely necessary. Thus the hydrochloric acid formed in this reaction can be scavenged by a nonnucleophilic amine such as triethylamine or pyridine, for example. In that case the amount of nonnucleophilic amine is preferably 0 to 10 mol. eq., more preferably 0.5 to 1.5 mol. eq., based in each case on the perylene derivative. A further possibility is to react nonnucleophilic amines, including short nonnucleophilic amines where appropriate, in the same way as relatively unreactive long-chain OH-terminated polymers.

A possible byproduct of the preparation either of the corresponding acid esters or of the corresponding acid amides is the free acid, through hydrolysis of the acid chlorides. This unwanted byproduct becomes soluble in water at neutral to alkaline pH. The compounds described are therefore freed of these byproducts, and also of any amine hydrochlorides formed, by washing with water. A red color in the water running off is indicative of the free acids: when the wash water is no longer colored, free acid is no longer present.

The present invention additionally provides the perylene derivatives described by the above process.

The present invention also provides for the use of compounds composed of a parent structure and of at least one substituent covalently bonded to said structure,
the parent structure being a polycyclic, substantially aromatic hydrocarbon and selected in particular from the group consisting of naphthalene derivatives, phenalene derivatives, perylene derivatives, pyrene derivatives, fluoranthene derivatives, fluorene derivatives, heptalene derivatives, indene derivatives, phenanthrene derivatives, anthracenyl derivatives, and acenaphthene derivatives, and
the substituent or substituents being able to exert a sterically and/or electrostatically stabilizing effect on a pigment;
as pigment dispersants.

The present invention also provides, accordingly, for the use of the above-described perylene derivatives of the invention as pigment dispersants.

By dispersants are meant substances which facilitate the dispersing of particles in a fluid dispersion medium. The dispersants lower the interfacial tension between the two components and thereby induce wetting. A large number of synonymous names are in use for dispersants, examples being additives, wetting agents, detergents, suspension aids, emulsifiers, dispersing agents, and so on. Additionally, the free surfaces brought about during the pigment dispersing operation are stabilized.

The perylene derivatives of the invention are useful as pigment dispersants for a multiplicity of different pigments. As regards the pigments, refer to DE-A 199 02 907, already mentioned, whose entire disclosure content is included by reference in the present invention.

The perylene derivatives of the invention are particularly suitable for the following pigments:

| | |
|---|---|
| Quinacridone pigments | P.R.122; P.R.202, P.V.19 |
| Quinophthalone pigments | P.Y.138 |
| Isoindoline pigments | P.O.69, P.O.61, P.Y.139, P.Y.185 |
| Perylene pigments | P.R.123, P.R.149, P.R.178, P.R.179, P.R.224, P.V.29 |

| -continued | |
|---|---|
| Phthalocyanine pigments | P.B.15, P.B.15:1, P.B.5:2, P.B.15:3, P.B.15:4, P.B.15:6, P.B.16, P.G.7, P.G.36 |
| Indanthrone pigments | P.B.60 and P.B.64 |
| Dioxazine pigments | P.V.23 |
| Triarylcarbonium pigments | P.V.27 |
| Disazo pigments | P.O.34, P.R.144, P.R.166, P.Y.12, P.Y.13, P.Y.17, P.Y.83, P.Y.113, P.Y.126, |
| Monoazo pigments | P.O.5, P.O.36, P.O.67, P.R.1, P.R.2, P.R.3, P.R.48:4, P.R.49, P.R.52:2, P.R.53, P.R.57:1, P.R.251, P.R.112, P.R.170, P.R.184, P.R.190 |
| Thioindigo pigments | P.R.88 |
| Metal complex pigments | P.Y.117, P.Y.153, P.Y.177 |
| Perinone pigments | P.O.43, P.R.194 |
| Flavanthrone pigments | P.Y.24 |
| Anthraquinone pigments | P.Y.147, P.V.31 |

Further examples are given in W. Herbst, K. Hunger, *Industrial Organic Pigments*, VCH Weinheim, 1993, the entire disclosure content of which is included by reference.

The present invention further provides pigment preparations comprising
(a) at least one organic pigment and
(b) at least one compound composed of a parent structure and at least one substituent covalently bonded to said structure,
the structure being a polycyclic, substantially aromatic hydrocarbon and being selected in particular from the group consisting of naphthalene derivatives, phenalene derivatives, perylene derivatives, pyrene derivatives, fluoranthene derivatives, fluorene derivatives, heptalene derivatives, indene derivatives, phenanthrene derivatives, anthracenyl derivatives, and acenaphthene derivatives, and
the substituent or substituents being able to exert a sterically and/or electrostatically stabilizing effect on a pigment; as pigment dispersant.

The pigment preparations of the invention generally comprise at least one above-described perylene derivative of the invention.

In the pigment preparations of the invention, in the case of the sterically stabilizing radicals, there is in general from 2 to 50% by weight, preferably from 2 to 30% by weight, more preferably from 2 to 20% by weight of pigment dispersant, based on the pigment. In the pigment preparations of the invention, in the case of the electrostatically stabilizing radicals, there is preferably from 0.5 to 5% by weight, more preferably from 0.5 to 4% by weight, very preferably from 0.5 to 3% by weight of pigment dispersant, based on the pigment.

As regards the selection of pigments for the pigment preparations of the invention, refer to remarks above regarding the use of the perylene derivatives of the invention.

The pigment preparations of the invention preferably comprise a red organic perylene pigment, especially P.R. 179.

The pigment preparations of the invention comprise the pigments preferably in finely divided form. In this case the average primary particle size is generally less than 300 nm, preferably less than 200 nm, more preferably less than 100 nm. The pigment preparations of the invention are particularly suitable for producing transparent colors.

Besides the pigment and pigment dispersant, the pigment preparations of the invention may comprise further, customary additives, such as fillers, standardizers, surface-active agents, resins, defoamers, antidust agents, extenders, dispersing additives, shading colorants, preservatives, drying retardants, and, where appropriate, block copolymers and polymer with polar anchor groups, for example. These additives may serve, for example, to improve pigment wetting or pigment dispersing or as plasticizers or film formers.

The pigment preparations of the invention comprise pigments generally in an amount of from 0.5 to 40% by weight, preferably from 0.5 to 30% by weight, more preferably from 0.5 to 5% by weight, based in each case on the pigment preparation of the invention.

Where additives are present in the pigment preparations of the invention their amount including solvent, is generally from 60 to 99.5% by weight, preferably from 70 to 99.5% by weight, more preferably from 95 to 99.5% by weight, based in each case on the pigment preparation of the invention.

Suitable surface-active agents include customary anionic, cationic or nonionic surfactants or mixtures of these agents. Examples of anion-active substances are fatty acid taurides, fatty acid N-methyltaurides, fatty acid ethionates, alkylbenzenesulfonates, alkylnaphthalenesulfonates, alkylphenol polyglycol ether sulfates and fatty alcohol polyglycol ether sulfates, fatty acids, e.g., palmitic, stearic, and oleic acid, soaps, e.g., alkali metal salts of fatty acids, naphthenic acids, and resin acids, e.g., abietic acid, alkali-soluble resins, e.g., rosin-modified maleate resins, and condensation products based on cyanuric chloride, taurine, N,N-dialkyl-aminoalkylamine, such as N,N-diethylaminopropylamine and p-phenylenediamine, for example; preference is given to resin soaps, i.e., alkali metal salts of resin acids. Suitable cation-active substances include, for example, quaternary ammonium salts, fatty amine oxyethylates, fatty amine polyglycol ethers, and fatty amines. Suitable nonionogenic substances include, for example, amine oxides, fatty alcohol polyglycol ethers, fatty acid polyglycol esters, and alkylphenol glycol ethers.

Polymers as additives of the invention are, for example, polyolefins, polyesters, polyethers, polyamides, polyurethanes, polyvinyl ethers, polyacrylates, and copolymers thereof. Examples of suitable anchor groups are amine groups and ammonium groups, carboxylic acid groups and carboxylate groups, sulfonic acid groups and sulfonate groups, and phosphoric acid groups and phosphonate groups.

Preferred polymers are those with nitrogen-containing anchor groups, especially amine groups and polyalkyleneimine groups, and also block copolymers with polyalkyleneimines such as polyethyleneimines, for example. Additives of this kind are known to the skilled worker. They are largely available commercially (e.g., Solspere® from Avecia, Disperbyk® from Byk) and described in numerous instances, for example, in Journal of Coating Technology 58 (1986), 71, in Journal of Oil and Colour Chemical Association 1998, 293 and 1991, 204, in DE-A 21 62 484, DE-A 22 64 176, DE-A 28 07 362, DE-A 28 30 860 and in EP-A 0 189 385, the entire disclosure content of which is included by reference.

The pigment preparations of the invention are generally solid systems of free-flowing powderous nature or granules.

The pigment preparations of the invention can be mixtures of one or more pigments, preferably one or two pigments, with one or more, preferably one or two, of the pigment dispersants of the invention. The pigment preparations may also include noninventive pigment dispersants in addition.

The invention further provides a process for preparing a pigment preparation of the invention which involves mixing at least one compound, as pigment dispersant, which is composed of a parent structure and at least one substituent covalently bonded to said structure, the parent structure being a polycyclic, substantially aromatic hydrocarbon and being selected in particular from the group consisting of naphthalene derivatives, phenalene derivatives, perylene derivatives, pyrene derivatives, fluoranthene derivatives, fluorene derivatives, heptalene derivatives, indene derivatives, phenanthrene derivatives, anthracenyl derivatives, and acenaphthene derivatives, and it being possible for the substituent or substituents to exert a sterically and/or electrostatically stabilizing effect on a pigment and the organic pigment or allowing them to act on one another at any desired point in time during the operation of preparing them.

In this process of the invention the abovementioned perylene derivatives of the invention are generally used.

Generally in the process of the invention the pigment dispersant and the organic pigment are mixed with one another in the form of dry powders.

The operation of preparing a pigment embraces its synthesis, possibly fine division, e.g., by grinding or reprecipitation, optionally finishing, and isolation as a presscake or as dry granules or powder. To prepare the pigment preparations of the invention the pigment dispersants can, for example, be added before or during the pigment synthesis, immediately before or during fine division or immediately before or during a subsequent finish. Temperatures of, for example, from 0 to 200° C. may occur in these operations. Naturally, the pigment dispersants can also be added in portions at different times.

The addition of the pigment dispersants in the course of a fine division can be made, for example, before or during the dry grinding of a crude pigment with or without additional grinding assistants on a roll mill or shrink mill, or before or during the wet grinding of a crude pigment in an aqueous, aqueous-organic or organic grinding medium, on a bead mill, for example. The precise grinding media are known to the skilled worker. Furthermore these grinding media are disclosed in DE-A 198 36 714, whose disclosure of content in this respect is included by reference in the present invention. In addition it is possible to add the dispersants of the invention to the pigment before or during an operation of kneading or wet coating.

It has proven equally appropriate to add the pigment dispersants before or after the finishing of the pigment in an aqueous, aqueous-alkaline, aqueous-organic or organic medium. The pigment dispersants may also be added to and incorporated into the water-moist pigment presscake prior to drying, in which case the pigment dispersants may themselves likewise be present in presscake form.

Further possibilities for preparing the pigment dispersants are kneading and subsequent drying; wet grinding and subsequent drying; wet grinding, filtration, and subsequent drying; stirred in corporation, filtration and subsequent drying.

In one preferred embodiment of the present invention powders or granules of the pigment dispersants are dry-mixed with the powder or granules of one or more pigments.

In accordance with the invention between 1 and 30 parts of the dispersants are modified with 100 parts by weight of the crude pigment.

The pigment preparations obtainable by the present invention are notable for their outstanding coloristic and rheological properties, high flocculation stability, high transparency, ready dispersibility, good gloss characteristics, high color strength, excellent fastness to overcoating and to solvent, and very good weatherfastness. They are suitable for use both in solventborne and in aqueous systems, i.e., they can be optimized both for solventborne and for aqueous systems.

The pigment preparations prepared in accordance with the invention can be used as colorants for pigmenting high molecular mass organic materials of natural or synthetic origin in the form of plastic masses, melts, spinning solutions, varnishes, paints, toners or printing inks.

Examples of high molecular mass organic materials for which the pigment preparations of the invention are particularly suitable are cellulose ethers and cellulose esters, such as ethylcellulose, nitrocellulose, cellulose acetate or cellulose butyrate, natural resins or synthetic resins, such as addition-polymerization resins or condensation resins, e.g., amino resins, especially urea and melamine formaldehyde resins, acrylic resins, alkyd resins, phenolic resins, polycarbonates, polyolefins, polystyrenes, polyvinyl chlorides, polyalkylenes, polyacrylonitriles, polyacrylates, polyamides, polyurethanes or polyesters, and copolymers thereof, rubber, casein, silicone and silicone resins, in each case individually or in mixtures.

The high molecular mass organic compounds may be in the form of a plastic mass or melt or in the form of spinning solutions, varnishes, paints or printing inks. Depending on the intended use it is found advantageous to utilize the pigment preparations of the invention as a blend or in the form of a prepared formulation or dispersions. Based on the high molecular mass organic material to be pigmented the pigment preparations of the invention are used in an amount of in general from 0.05 to 50% by weight, preferably from 0.1 to 30% by weight, more preferably from 1 to 10% by weight.

The pigment preparations of the invention are suitable in general for producing pigment dispersions, preferably paint materials, more preferably high-solids acrylic resin baking enamels, and solvent- or water-based paint pastes.

The present invention further provides pigment dispersions which comprise at least one perylene derivative of the invention or at least one pigment preparation of the invention.

The present invention displays a number of advantages over the prior art:

The perylene derivatives of the invention are easy and inexpensive to prepare and the pigment preparations of the invention are distinguished by good performance properties. Thus they bring about high dispersibility and flocculation stability in the application medium and, furthermore, outstanding gloss and outstanding coloristics. The theological properties of the pigment can be enhanced through the use of the pigment dispersants of the invention.

Further embodiments, modifications, and variations, and also advantages, of the present invention are immediately recognizable to the skilled worker on reading the description and are realizable by the skilled worker without departing the scope of the present invention.

The present invention is illustrated using the examples, which do not, however, in any way restrict the invention.

EXAMPLES

Preparation of perylene-3,4-dicarboximide 9-sulfonyl chloride 16.1 g (0.05 mol) of perylenedicarboximide are stirred slowly at room temperature into 67 g of chlorosulfonic acid and the mixture is heated to 55° C. and stirred at this temperature for three hours. Then 11.0 g of thionyl chloride are slowly added dropwise at this temperature and the reaction mixture is stirred for a further 15 minutes. It is cooled to room temperature and filtered with suction over a D4 glass frit, the solid product is washed quickly with a little ice-water, and then the water is displaced using acetone. The acetone-moist presscake is either reacted further immediately or dried under reduced pressure and stored under an inert gas atmosphere.

Yield 14.8–17.6 g, 71–84%

Preparation of perylene-3,4-dicarboximide 9-carbonyl chloride

Perylene-3,4-dicarboximide 9-carboxylic acid is prepared in accordance with CAS75:140549j (1971). Conversion of the carboxylic acid thus obtainable to the carbonyl chloride is accomplished by suspending 18.2 g (0.05 mol) of the carboxylic acid in 100 ml of $CH_2Cl_2$ and adding 8.85 g (0.075 mol) of thionyl chloride at room temperature. The mixture is refluxed for 5 hours, after which residues of the thionyl chloride and of methylene chloride are distilled off. The red solid is processed further without additional characterization.

Predominantly Electrostatically Stabilizing Radicals

Example 1

Perylene-3,4-dicarboximide 9-(N,N-dimethylaminopropyl)sulfonamide (Dispersant 1)

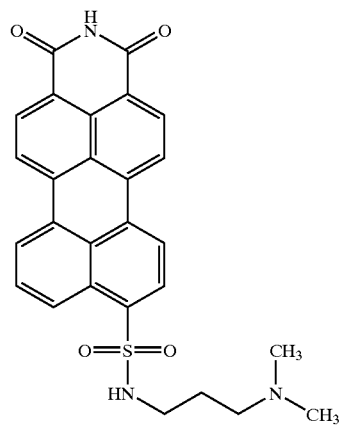

10.2 g (0.10 mol) of N,N-dimethylaminopropylamine and 50.8 g (1.0 mol) of triethylamine are stirred into 200 ml of dichloromethane at 0° C. The above-described acetone-moist presscake of perylene-3,4-dicarboximide 9-sulfonyl chloride is slowly introduced. The temperature rises to 10° C. The reaction mixture is stirred overnight and then the solvent and the triethylamine are evaporated on a rotary evaporator. 10.0 g of the residue are stirred extractively in 100 ml of water for three hours, the solid product is isolated by filtration, and the presscake is dried in a drying cabinet. This gives 0.59 g (39%) of a red solid:

Rf (dioxane:triethylamine:water=20:4:1)=0.7 m.p. 246–248° C. $^1$H-NMR(d6-DMSO): δ=11.80–11.55 (bs, 1H, OCNHCO), 8.60 (pd, 1H, Ar—H), 8.55 (pd, 2H, Ar—H), 8.49–8.46 (m, 2H, Ar—H), 8.20 (pd, 2H, Ar—H), 7.82 (pt, 1H, Ar—H), 2.98 (dd, 2H, CH$_2$), 2.21 (dd, 2H, CH$_2$), 2.05 (s, 6H, CH$_3$), 1.50 (dd, 2H, CH$_2$—CH$_2$—CH$_2$) ppm. SO$_2$NH not observed.

Example 2

Perylene-3,4-dicarboximide 9-(N,N-diethylaminoethyl)sulfonamide (Dispersant 2)

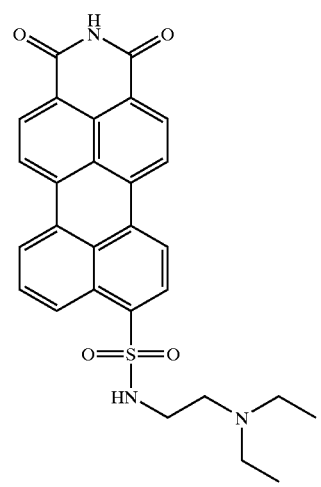

The above-described acetone-moist presscake of perylene-3,4-dicarboximide 9-sulfonyl chloride is added slowly at 0° C. to a mixture of 200 ml of dichloromethane and 11.6 g (0.1 mol) of N,N-diethylaminoethylamine and 50.8 g (1.0 mol) of triethylamine at 0° C. The reaction mixture is stirred overnight and then the solvent and the triethylamine are evaporated on a rotary evaporator. The residue is stirred extractively in 180 ml of water for three hours, the solid product is isolated by filtration and the presscake is dried in a drying cabinet. This gives 15.2 g (61%) of a red solid.

Rf (dioxane:triethylamine:water=20:4: 1)=0.8 m.p. 238–240° C. $^1$H-NMR(d6-DMSO): δ=11.90–11.65 (bs, 1H, OCNHCO), 8.62 (pd, 1H, Ar—H, 8.50 (pd, 2H, Ar—H), 8.48–8.46 (m, 2H, Ar—H, 8.25 (pd, 2H, Ar—H), 7.95 (pt, 1H, Ar—H), 3.24 (dd, 2H, CH$_2$), 2.65 (dd, 2H, CH$_2$), 2.45 (q, 4H, CH$_2$—CH$_3$), 2.25 (bs, 1H, SO$_2$NH, 1.10 (t, 6H, CH$_2$—CH$_3$) ppm.

Example 3

Perylene-3,4-dicarboximide
9-(N-aminoethylpiperazyl)sulfonamide
(Dispersant 3)

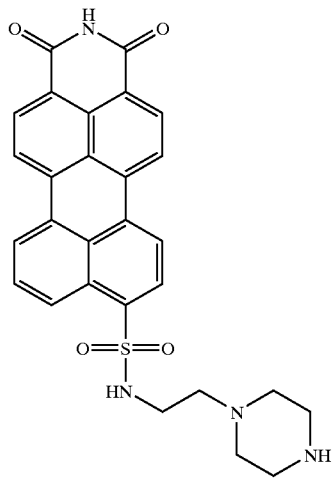

The above-described acetone-moist presscake of perylene-3,4-dicarboximide 9-sulfonyl chloride is added slowly at 0° C. to a mixture of 200 ml of dichloromethane and 11.6 g (0.1 mol) of N,N-diethylaminopiperazine and 50.8 g (1.0 mol) of triethylamine. The reaction mixture is stirred overnight and then the solvent and the triethylamine are evaporated on a rotary evaporator. The residue is stirred extractively in 230 ml of water overnight, the solid product is isolated by filtration and the presscake is dried in a drying cabinet. This gives 10.4 g (21%) of a red solid.

Rf (dioxane:triethylamine:water=20:4:1)=0.55 m.p. 220° C. $^1$H-NMR(d6-DMSO): δ=11.50–11.30 (bs, 1H, OCN HCO), 8.70 (pd, 1H, Ar—H, 8.48 (pd, 2H, Ar—H, 8.40–8.8.35 (m, 2H, Ar—H, 8.$\overline{25}$ (pd, 2H, Ar—H, 7.95 (p̄t, 1H, Ar—H), 3.30 (m, 2$\overline{H}$, C$\underline{H}_2$), 2.68–2.62 (m, 6$\overline{H}$, C$\underline{H}_2$), 2.48–2.4$\overline{0}$ (m, 2H, C$\underline{H}_2$) ppm; SO$_2$N$\underline{H}$ not observed.

Example 4

Perylene-3,4-dicarboximide
9-(N,N,-dimethylaminopropyl)carboxamide
(Dispersant 4)

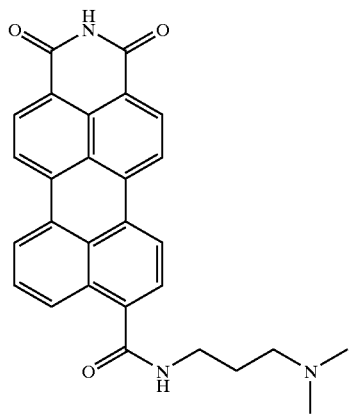

5.1 g (0.05 mol) of N,N-dimethylaminopropylamine and 25.4 g (0.5 mol) of triethylamine are stirred into 200 ml of dichloromethane at 0° C. The above-described red solid (0.05 mol) of perylene-3,4-dicarboximide 9-carbonyl chloride is slowly introduced. The reaction mixture is stirred overnight and the solvent and the triethylamine are evaporated on a rotary evaporator. The residue is stirred extractively in 100 ml of Na$_2$CO$_3$ solution for three hours, the solid product is isolated by filtration and washed repeatedly with water, and the presscake is dried in a drying cabinet. This gives 10.78 g (48%) of a red solid.

R$_f$ (dioxane:triethylamine:water=20:2:1)=0.4 $^1$H-NMR (d6-DMSO): δ=11.85–11.60 (bs, 1H, OCNHCO), 8.50 (pd, 1H, Ar—H), 8.45 (pd, 2H, Ar—H), 8.40–8.$\overline{32}$ (m, 2H, Ar—H), 8.15 (p̄d, 2H, Ar—H), 8.0 (s, 1H, CONH), 7.88 (pt, 1H, Ar—H), 3.10 (dd, 2H, $\overline{C}$H$_2$), 2.30 (dd, 2$\overline{H}$, C$\underline{H}_2$), 2.15 (s, 6H, C$\underline{H}_3$), 1.55 (dd, 2H, $\overline{C}$H$_2$—C$\underline{H}_2$—CH$_2$) ppm.

Example 5

Performance Test with Dispersants 1 to 4
(Examples 1 to 4)

Dry mixes are produced, each containing 7.50 g of a transparent commercially customary pigment P.R. 179 and 225 mg of a perylene derivative as prepared in one of examples 1 to 3. The control sample is the commercially customary transparent P.R. 179. Dispersing is carried out in a 100 ml glass bottle using 27 ml of glass beads with a diameter of 3 mm. Addition of 23.3 g of a high-solids varnish (acrylic resin with xylene and butyl acetate solvents) is followed by shaking with a conventional Scandex apparatus for 2 hours. After standing for 24 hours the control sample has a visual fluidity of 1 (the paste has set and cannot be removed from the glass vessel), whereas the samples containing the pigment dispersants of the invention from examples 1 to 3 are of low viscosity and can be removed from the glass vessel. The paint dispersions prepared with the pigment dispersants of the invention from examples 1 to 3, in a white reduction, are stronger in color, more yellow, more transparent, and have a lower yield point.

| Sample | CE | dH | DC | dL | DdE | vis. yield point |
|---|---|---|---|---|---|---|
| Control paste | 100 | 0.0 | 0.0 | 0.0 | 0.0 | 1 |
| Paste disp. 1 | 90 | 0.8 | 2.0 | −2.0 | −3.0 | 3–4 |
| Paste disp. 2 | 85 | 1.0 | 2.2 | −2.5 | −3.5 | 4 |
| Paste disp. 3 | 88 | 0.6 | 1.8 | −1.8 | −4.4 | 4 |
| Paste disp. 4 | 95 | 0.3 | 0.8 | −0.7 | −2.3 | 3 |

Predominantly Sterically Stabilizing Radicals

Example 6 a) Preparation of a Methacrylate Copolymer from MMA and BMA

A 1l stirred apparatus consisting of four-necked flask, stirrer, condenser, thermometer and two metering pumps for the feeds is charged with 175.0 g of tetrahydrofuran and this initial charge is brought to boiling temperature (bath temperature 80° C.). Subsequently the two feeds, consisting of feed 1a (159.0 g) of methyl methacrylate and 159.0 g of butyl methacrylate and feed 1b (6.60 g) of 2-mercaptoethanol, 0.80 g of α,α'-azoisobutyronitrile and 30.0 g of tetrahydrofuran, are commenced at the same time and, by way of the metering pumps, the solutions are metered in continuously over the course of 120 minutes. The reaction is held at an external temperature of 80° C. until the monomer content has fallen to below 3% (as determined by gas chromatography.

b) Reaction with perylene-3,4-dicarboximide 9-carbonyl chloride (Dispersant 5)

Perylene-3,4-dicarboximide 9-carbonyl chloride prepared as described above (0.05 mol) is suspended in 100 ml of THF in the presence of 5.05 g (0.05 mol) of triethylamine and this suspension is added to half of the polymer solution, cooled at 0° C. After it has been added the suspension is refluxed for 24 hours. The THF is removed under reduced pressure and the residue is taken up in 500 ml of butyl acetate and 75 ml of water. The organic phase is washed repeatedly with water until it appears colorless. The organic phase is dried over $MgSO_4$ and the solvent is removed under reduced pressure. This gives 175 g of a red solid.

Rf (dioxane:water:$NEt_3$=20:1:4)=0.9.

Example 7

Reaction product of perylene-3,4-dicarboximide 9-sulfonyl chloride with polyester-grafted polyethyleneimine (Dispersant 6)

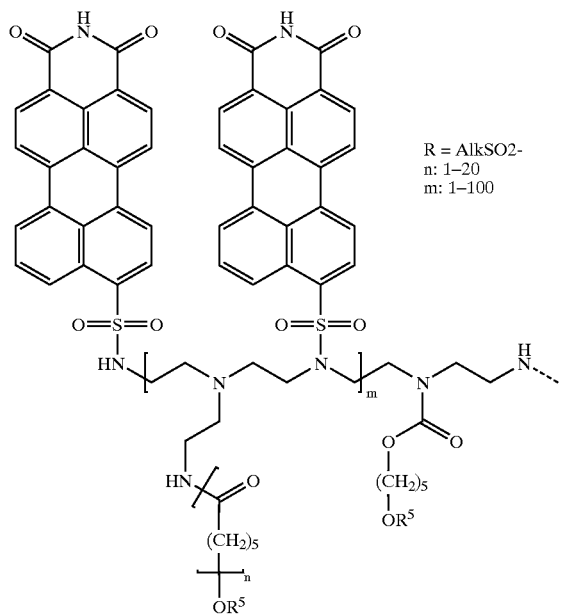

14.7 g (8.6 meq) of a polyester-grafted polyethyleneimine (amine number 33.5 mg KOH/g) and 19.2 g of triethylarine are dissolved in 150 ml of DMF and the solution is heated to 70° C. before 2.6 g (6.2 mmol) of the dried perylene-3,4-dicarboximide 9-sulfonyl chloride are added. The reaction mixture is stirred at 70° C. for four hours before the DMF is removed under reduced pressure (200 mbar). The residue is finely powdered, stirred with water, filtered over a D4 glass frit, and washed (about 2 l) until the runoff is colorless. This gives 14.7 g of a red solid (89%).

The absence of a broad signal in the $^1H$-NMR($CDCl_3$) between 5.4 and 4.9 ppm indicates the absence of amine NH groups, which have reacted to the sulfonamide. A thin-layer chromatogram (TLC) (silica gel dioxane:water:triethylamine=20:1:4) shows traces of the free sulfonic acid (Rf=0.54), but essentially a new compound (Rf=0.98).

Example 8

Performance Test with Dispersants 5 and 6 (Example 6 and 7)

A dry mix is prepared from 7.50 g of a transparent commercially customary pigment P.R. 179 and 1.2 g of dispersant 5 or of dispersant 6. The control sample is a mixture of 7.50 g of the commercially customary transparent pigment, to which 1.2 g of xylene are added before the varnish is added (control). Dispersing takes place in a 100 ml glass bottle using 27 ml of glass beads having a diameter of 3 mm. Addition of 23.3 g of a high-solids varnish (acrylic resin with xylene and butyl acetate solvents) is followed by shaking for 2 hours with a conventional Skandex apparatus. After standing for 24 hours the control sample has a visual fluidity of 1 (paste has set and cannot be removed from the glass vessel), whereas the samples containing dispersant 5 and dispersant 6 are of high and low viscosity, respectively, but can both be removed from the glass vessel. The control, in the white reduction, is weaker in color, bluer, and less chromatic than the paint pastes prepared using dispersant 5 and 6.

| Sample | CE | dH | dC | dL | ddE | vis. yield point |
|---|---|---|---|---|---|---|
| Control paste | 100 | 0.0 | 0.0 | 0.0 | 0.0 | 1 |
| Paste disp 5 | 92 | 0.6 | 2.2 | −2.0 | −3.0 | 3 |
| Paste disp 6 | 80 | 1.1 | 3.9 | −4.0 | −6.0 | 4 |

Example 9

Reaction product of perylene-3,4-dicarboximide 9-sulfonyl chloride with methyl-capped polyethylene glycol MeO—($CH_2$—$CH_2$—O)$_{23}$—OH (Dispersant 7)

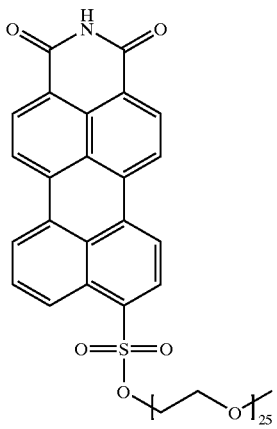

4.19 g (0.01 mol) of perylene-3,4-dicarboximide 9-sulfonyl chloride are added to a solution of 10.0 g (0.01 mol) of MeO—(CH$_2$—CH$_2$—O)$_{23}$—OH (Pluriol A1000E) and 10.1 g (0.1 mol) of triethylamine. The reaction mixture is heated to 70° C. and stirred at this temperature for four hours. Subsequently the DMF is evaporated off under reduced pressure. This gives 18.2 g of a sticky residue which is processed further without additional purification. TLC (silica gel dioxane:water:triethylamine=20:1:4) shows traces of the free sulfonic acid (Rf=0.54), but essentially a new compound (Rf=0.1).

Example 10

Performance Test of the Compound from Example 7

10.0 g (39% solids content) of a presscake of a commercially customary transparent pigment P.R. 179 are wet-ground with 1.0 g of the unpurified pigment dispersant from example 6 (dispersant 7) in a 100 ml glass vessel for 4 hours in a Skandex shaker using SAZ beads (1 mm diameter). After the SAZ beads have been separated off the pigment is isolated by filtration. After three days of filtration a moist presscake is obtained which after drying in a drying cabinet gives 4.60 g of a solid. After careful trituration of the pigment pieces they are compared with the dried and ground presscake in a commercial PU aqueous basecoat material (polyester, polyurethane, water, butyl glycol).

For this purpose 3.5 g of the control sample (dried and ground presscake) and 3.5 g of the surface-modified above-mentioned pigment sample are dispersed with 18.5 g of an aqueous dispersing varnish (PU) in a 100 ml glass bottle with 32 ml of SAZ beads on a Skandex shaker for 18 minutes. 2.0 g of the paste are mixed with 2.0 g of a letdown component (PU-based) and a white reduction is prepared. The remainder of the pastes are dispersed for a total of three hours and in each case 2.0 g of the pastes are mixed with 2.0 g of the letdown component (PU-based) and a white reduction is prepared.

The surface-modified pigment sample has a lower dispersing hardness, a higher ultimate color strength, higher chroma, a more yellow shade, and a greater translucency.

| Sample | CE (18 min) | CE (3 h) | dH (3 h) | dC (3 h) | dL (3 h) | ddE (3 h) |
|---|---|---|---|---|---|---|
| Paste 8/control | 130 | 100 | 0.0 | 0.0 | 0.0 | 0.0 |
| Paste | 92 | 80 | 1.3 | 2.0 | -2.0 | -2.0 |

What is claimed is:

1. A perylene derivative of the formula (I)

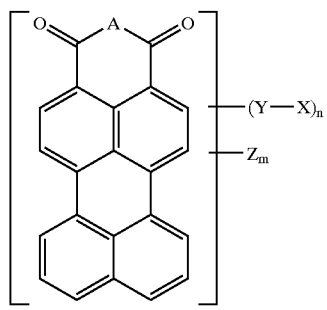

(I)

where

A has the definition O, CH$_2$ or NR$^1$ with R$^1$ being H, aryl, aralkyl, heteroaryl, cycloalkyl, C$_1$–C$_{22}$ alkyl, Y, each identical or different, is —CO$_2$, —CONR$^2$, —SO$_3$ or —SO$_2$NR$^2$, R$^2$ being H, aryl, aralkyl, heteroaryl, cycloalkyl, C$_1$–C$_{22}$ alkyl, alkylamine, in which the amine function may carry one or more further substituents and may be part of a polyamine, X, each identical or different, is bonded covalently to the perylene derivative and is selected from the group consisting of sterically stabilizing substituents and electrostatically stabilizing substituents, at least one X being selected from the sterically stabilizing substituents, Z, each identical or different, represents where present one or more further substituents, selected from the group consisting of alkyl, alkoxy, and aryloxy groups and halogens, n is an integral number greater than or equal to 1, and m is an integral number greater than or equal to 0; and wherein the sterically stabilizing substituents are selected from the group consisting of polymers based on alkylene oxides, polymers based on polyesters, polymers based on polyacrylates, polymers based on alkyl sulfides, and polymers based on alkyl compounds.

2. A perylene derivative as claimed in claim 1, wherein the polymers are block (co)polymers.

3. A perylene derivative as claimed in claim 1, wherein the electrostatically stabilizing substituents contain ammonium groups and/or protonatable amino groups.

4. A perylene derivative as claimed in claim 1, wherein in the formula (I) n=1 and m=0 and the perylene derivative is of the formula (III)

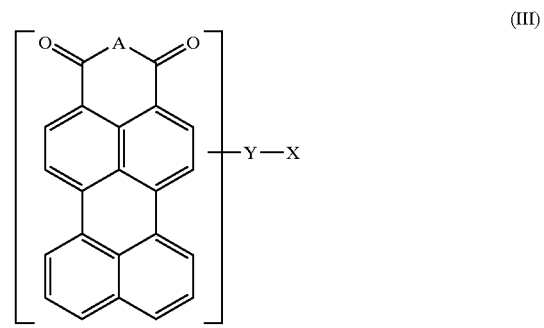

(III)

where in the formula (III)

A is NH,

Y is —CONH, —SO$_3$ or —SO$_2$NH,

X is a substituent which includes a protonatable amino group, or

X is C$_1$–C$_{30}$ alkyl or C$_3$–C$_{30}$ alkenyl, it being possible for the carbon chain to be interrupted in each case by one or more groups —O—, —CO—O—, —O—CO— or —S— and each of which may be substituted by C$_1$–C$_6$ alkoxy, amino, hydroxyl, carboxyl groups and halogens, where R$^4$ is H, alkyl, cycloalkyl, aryl, heteroaryl or aralkyl.

5. A pigment preparation comprising
(a) at least one organic pigment; and
(b) the perylene derivative of claim 1 as pigment dispersant.

6. A pigment preparation as claimed in claim 5, wherein the pigment preparation contains from 2 to 50% by weight of pigment dispersant per g of pigment in the case of the sterically stabilizing substituents and from 0.5 to 5% by weight of pigment dispersant per g of pigment in the case of the electrostatically stabilizing substituents.

7. A pigment preparation as claimed in claim 5, wherein the at least one organic pigment is finely divided and has an average primary particle size of less than 300 nm.

8. A process for preparing the pigment preparation of claim 5, the process comprising
mixing at least one organic pigment and, as pigment dispersant, a perylene derivative of the formula (I)

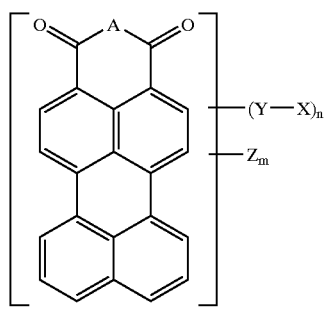

where
A has the definition O, $CH_2$ or $NR^1$ with $R^1$ being H, aryl, aralkyl, heteroaryl, cycloalkyl, $C_1$–$C_{22}$ alkyl,
Y, each identical or different, is —$CO_2$, —$CONR^2$, —$SO_3$ or —$SO_2NR^2$, $R^2$ being H, aryl, aralkyl, heteroaryl, cycloalkyl, $C_1$–$C_{22}$ alkyl, alkylamine, in which the amine function may carry one or more further substituents and may be part of a polyamine,
X, each identical or different, is bonded covalently to the perylene derivative and is selected from the group consisting of sterically stabilizing substituents and electrostatically stabilizing substituents, at least one X being selected from the sterically stabilizing substituents,
Z, each identical or different, represents where present one or more further substituents, selected from the group consisting of alkyl, alkoxy, and aryloxy groups and halogens,
n is an integral number greater than or equal to 1, and
m is an integral number greater than or equal to 0; and
wherein the sterically stabilizing substituents are selected from the group consisting of polymers based on alkylene oxides, polymers based on polyesters, polymers based on polyacrylates, polymers based on alkyl sulfides, and polymers based on alkyl compounds.

9. A process as claimed in claim 8, wherein the pigment dispersant and the organic pigment are mixed with one another in the form of dry powders.

10. A pigment dispersion, comprising at least one perylene derivative as claimed in claim 1.

11. A pigment dispersion, comprising at least one pigment preparation as claimed in claim 5.

12. A perylene derivative of the formula (IV)

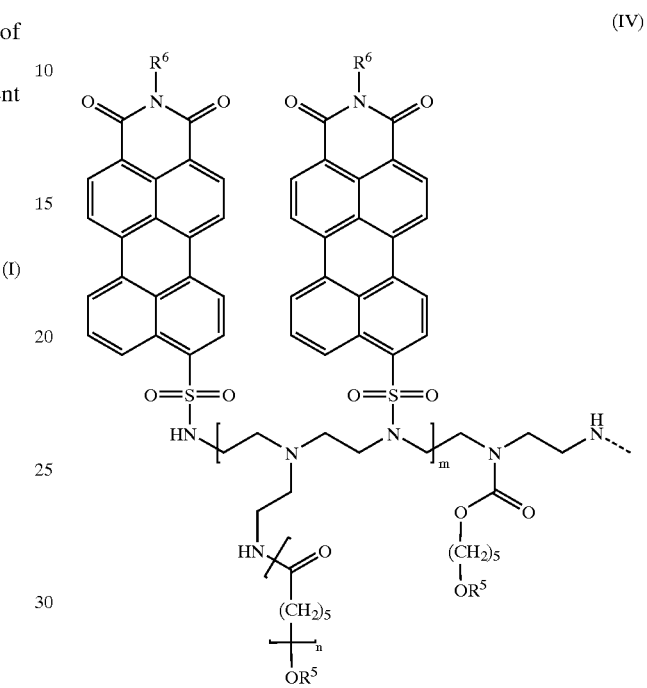

in which
m is an integral number from 1 to 100,
n is an integral number from 1 to 20,
$R^5$ is $C_{1-64}$-alkyl-$SO_2$, and
$R^6$ is H or $C_1$–$C_6$ alkyl.

13. A process for preparing a perylene derivative of the formula (I)

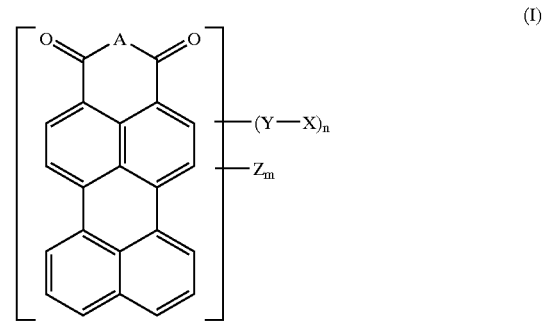

where
A has the definition O, $CH_2$ or $NR^1$ with $R^1$ being H, aryl, aralkyl, heteroaryl, cycloalkyl, $C_1$–$C_{22}$ alkyl, Y, each identical or different, is —CO$_2$, —CONR$^2$, —SO$_3$ or —SO$_2$NR$^2$, R$^2$ being H, aryl, aralkyl, heteroaryl, cycloalkyl, C$_1$–C$_{22}$ alkyl, alkylamine, in which the amine function may carry one or more further substituents and may be part of a polyamine, X, each identical or different, is a predominantly sterically stabilizing and/or electrostatically stabilizing substituent, Z, each identical or different, represents where present one or more further substituents, selected from the group consisting of alkyl, alkoxy, and aryloxy groups and halogens, n is an integral number greater than or equal to 1, and m is an integral number greater than or equal to 0, and wherein the predominantly sterically stabilizing and/or electrostatically stabilizing substituent is/are bonded covalently to the perylene derivative; and wherein a COCl- and/or SO$_2$Cl-substituted perylene derivative of the formula (V)

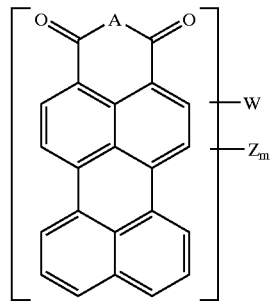

(V)

W=COCl or SO$_2$Cl in which A is O, CH$_2$ or NR$^1$ with R$^1$ being H, aryl, aralkyl, heteroaryl, cycloalkyl, C$_1$ to C$_{22}$ alkyl, Z, each identical or different, is where present one or more further substituents, selected from the group consisting of alkyl, alkoxy, and aryloxy groups and halogens, and m is an integral number greater than or equal to 0 is reacted with alcohols, thiols and/or amines.

* * * * *